United States Patent [19]

Hardy, Sr. et al.

[11] 4,034,023
[45] July 5, 1977

[54] PROCESS FOR PREPARING MIXED PHOSPHATE ESTER COMPOSITIONS

[75] Inventors: Donald Hardy, Sr., Yardley; Edward Francis Orwoll, Langhorne, both of Pa.

[73] Assignee: FMC Corporation, Philadelphia, Pa.

[22] Filed: May 5, 1975

[21] Appl. No.: 574,588

[52] U.S. Cl. .............................. 260/973; 260/963; 260/974; 260/975

[51] Int. Cl.² .................. C07F 9/11; C07F 9/12

[58] Field of Search .......... 260/973, 974, 975, 963

[56] References Cited

UNITED STATES PATENTS

| 2,504,121 | 4/1950 | Gamrath | 260/973 X |
| 2,596,141 | 5/1952 | Gamrath et al. | 260/973 X |
| 2,929,833 | 3/1960 | Orloff et al. | 260/973 |

OTHER PUBLICATIONS

Houben-Weyl, Methoden der Organischen Chemie, vol. 12/2 (1964) pp. 215, 216, 242, 310, 311 and 325-332.

*Primary Examiner*—Richard L. Raymond
*Attorney, Agent, or Firm*—Gary M. Nath; Frank Ianno

[57] ABSTRACT

Preparing mixed phosphate ester compositions consisting essentially of 10% to 19% tributyl phosphate, 62% to 80% dibutyl phenyl phosphate, and 10% to 19% butyl diphenyl phosphate which comprises forming a first reaction product by reacting phosphorus oxychloride with phenol in a molar ratio of 1:0.8 to 1.0 until less than 1% unreacted phenol is present in the reaction mixture, reacting the first reaction product with excess n-butanol at a temperature below 35° C to prepare a crude mixed phosphate ester composition comprising tributyl phosphate, dibutyl phenyl phosphate and butyl diphenyl phosphate, and purifying the crude composition leaving a substantially pure mixed phosphate ester composition.

5 Claims, No Drawings

PROCESS FOR PREPARING MIXED PHOSPHATE ESTER COMPOSITIONS

This invention relates to the preparation of a mixed phosphate ester composition consisting essentially of 10% to 19% tributyl phosphate, 62% to 80% dibutyl phenyl phosphate, and 10% to 19% butyl diphenyl phosphate.

A number of functional fluids containing esters of phosphoric acid are known which are intended for use in hydraulic power systems as lubricants and as force-transmission fluids for the transmission of power. Such fluids when employed in the hydraulic systems of aircraft must meet stringent functional and use requirements. These requirements include good lubricity to effectively lubricate the moving parts of the system, satisfactory viscosity at low as well as high temperatures at which the aircraft may operate, stability under conditions of use against loss of desired properties due to changes of pressure and temperature, non-corrosiveness to metal parts, non-deteriorating to gaskets and packings as well as low gasket and packing swelling tendency, and low ignition temperature, that is, non-flammable or fire-resistant. The fluid should also not cause dermal toxicity when personnel are brought into contact with the fluid.

A variety of methods have been proposed for the production of mixed alkyl/aryl phosphates. Such phosphates have been prepared by the reaction of an aliphatic alcohol with phosphorus oxychloride and the resulting phosphoryl dichloride is reacted with sodium phenoxide. These phosphates have also been prepared by reacting a trialkyl phosphate and/or thiophosphate with an aliphatic or aromatic hydroxy compound. These processes, however, have not proven to be commercially feasible for efficient and effective production of mixed butyl/phenol phosphate esters of high purity.

Another proposed procedure involves reacting 2 moles of phenol or similar hydroxyaryl compound with 1 mole of phosphorus oxychloride, removing the hydrogen chloride formed under vacuum, and then reacting the diphenyl phosphorylchloride with 1 mole of an aliphatic alcohol. This procedure is objectionable since the reaction is difficult to control, and excessive quantities of triaryl derivatives are formed resulting in impure and low product yields.

A process for preparing a mixed phosphate ester composition consisting essentially of 10% to 19% tributyl phosphate, 62% to 80% dibutyl phenyl phosphate, and 10% to 19% butyl diphenyl phosphate has been unexpectedly discovered which comprises: (a) reacting phosphorus oxychloride with phenyl in a molar ratio of 1:0.8 to 1.0 at a temperature of about 40° to about 100° C until less than 1% unreacted phenol is present in the reaction mixture while removing liberated hydrogen chloride from the reaction mixture to prepare a first reaction product comprising crude phenyl phosphorodichloridate, diphenyl phosphorochloridate and unreacted phosphorus oxychloride; (b) reacting the first reaction product with excess n-butanol under agitation at a temperature below 35° C for a sufficient time to prepare a second reaction product comprising crude tributyl phosphate, dibutyl phenyl phosphate, and butyl diphenyl phosphate; and (c) purifying the second reaction product by removing acid esters, acidic impurities, salts and unreacted n-butanol from the second reaction product thereby leaving a substantially pure mixed phosphate ester composition consisting essentially of 10% to 19% tributyl phosphate, 62% to 80% dibutyl phenyl phosphate, and 10% to 19% butyl diphenyl phosphate.

The mixed phosphate ester compositions prepared according to the process of this invention possess outstanding utility in functional fluids, and particularly in functional fluids employed in aircraft hydraulic systems.

According to the process of the invention, phosphorus oxychloride is reacted with phenol to prepare a first reaction product comprising crude phenyl phosphorodichloridate, diphenyl phosphorochloridate and unreacted phosphorous oxychloride. The reactants must be employed in the reaction mixture in amounts that provide a molar ratio of phosphorus oxychloride to phenol of 1:0.8 to 1.0. Only by carefully controlling the molar ratio of phosphorus oxychloride to phenol in the first reaction step are the mixed phosphate ester compositions of this invention produced. In addition, the reaction must be carried out until less than 1% unreacted phenol remains in the reaction mixture. If the phenol content is not less than 1% upon completion of the reaction, the specific amounts of the particular phosphate esters will not be produced.

The reaction is carried out at a temperature below about 100° C, at atmospheric pressure or under reduced pressure, in order to promote efficient removal of liberated hydrogen chloride and condensation of evolved phosphorus oxychloride from the hydrogen chloride vent steam. Excellent results are realized by running the reaction at atmospheric pressure whereby removal of up to 99% hydrogen chloride is routinely achieved. Reaction temperatures of about 40° to about 100° C are preferred, with temperatures of about 50° to about 60° C particularly preferred. Depending upon the reaction temperature and pressure, the reaction time varies from about 4 to about 30 hours. At the particularly preferred temperature range and atmospheric pressure, the reaction is completed in 5 to 12 hours.

Catalysts such as aluminum chloride or other metal halides or copper powder may be added to the reaction mixture to facilitate splitting off of the hydrogen chloride, and to speed up the reaction.

Upon completion of the first reaction, the first reaction product comprising the mixed chloridates and untreated phosphorus oxychloride is mixed and reacted with excess n-butanol. To maximize product yields and reduce the amount of phosphorus lost in waste water, at least two (2) moles of n-butanol per replaceable chlorine is used so that at least one (1) mole of n-butanol is present per mole of hydrogen chloride formed during the reaction. The presence of excess n-butanol during the reaction results in a protective effect probably due to solvation or partial hydrogen bonding, such as by forming an oxonium salt, such as

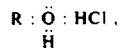

which engages the hydrogen chloride and limits hydrogen chloride attack of the neutral ester product from which a partial phosphoric acid ester and an alkyl halide are obtained. Because of this protective effect, removal of hydrogen chloride from the reaction mixture is not necessary thereby permitting the reaction to be performed under atmospheric pressure or under slightly reduced pressure.

The first reaction product is preferably slowly added to the n-butanol while the reaction mixture is agitated to assure adequate contact between the hydrogen chloride produced and the n-butanol. The ingredients must be mixed and reacted in the cold, that is at a temperature below 35° C, during the entire reaction to prevent product loss due to acid hydrolysis. Preferably, the reaction temperature is maintained at about 15° C to 20° C while the first reaction product is added to the n-butanol. Upon completion of the addition, the reaction temperature is preferably raised to and maintained at about 20° to 30° C until the reaction is complete. Temperatures below 0° C, while usable, prolong the reaction time; whereas temperatures above 35° C increase product losses due to acid hydrolysis. The reaction is completed in about 10 to 20 hours. Longer reaction times result in decreasing product yields because of competitive side reactions, that is the reaction between hydrogen chloride and the neutral ester product.

At the completion of the reaction, the second reaction product comprises tributyl phosphate, dibutyl phenyl phosphate and butyl diphenyl phosphate along with unreacted butanol, by-product hydrogen chloride and small amounts of butyl chloride, free phenol, aluminum salts and secondary acid phosphate esters. This material is purified to leave a substantially pure mixed phosphate ester composition consisting essentially of 10% to 19% tributyl phosphate, 62% to 80% dibutyl phenyl phosphate, and 10% to 19% butyl diphenyl phosphate having an alkyl/aryl molar ratio of 1.85 to 2.35.

The second reaction product is preferably purified by contacting the reaction product with a strong caustic solution to provide an excess of caustic, solvent stripping the caustic treated material, treating the solvent stripped material with a dilute caustic solution, and finally water washing to remove residual caustic.

The second reaction product is initially contacted with a strong aqueous caustic solution, preferably a 15 to 25 weight % sodium hydroxide solution to assure the presence of excess caustic at a temperature below 35° C, and preferably between 0° and 30° C, while mixing to avoid product decomposition. A sufficient amount of caustic must be present so that the resulting aqueous phase has a pH value above 10.5, and preferably above 11.0. By keeping the pH value of the aqueous phase above 10.5 the catalyst is extracted into the aqueous phase while maintaining n-butanol solubility therein at a very low level. For example, when aluminum chloride is employed as the catalyst, it is extracted as the soluble aluminate ($AlO_2^-$). Contacting the second reaction product in this manner results in removing hydrogen chloride, free phenol, and some of the acidic partial esters of phosphoric acid from the organic phase, which materials are the major product impurities.

Following caustic treatment, the organic phase of the two-phase system is separated from the aqueous phase containing dissolved impurities by decantation or by other conventional separating methods. The organic phase is then heated under vacuum at a temperature sufficient to distill off unreacted butanol and some butyl chloride. Preferred temperatures are between 50° and 150° C and most preferably between 70° and 100° C, at 5 to 100 mm Hg.

After solvent stripping, the residual crude phosphate ester product contains white solids, mostly sodium chloride and some crystallized sodium salts of partial esters of phosphoric acid. This product is contacted, preferably by washing with a dilute aqueous caustic solution, preferably a 0.5 to 5.0 weight % sodium hydroxide solution, at a temperature from 20° to 40° C to remove the major portion of the acidic partial esters of phosphoric acid and the solid impurities. The resulting color-free mixed phosphate ester composition is contacted with water at a temperature from 20° to 80° C to remove residual caustic.

The purified mixed phosphate ester composition can be optionally dehydrated by conventional procedures to remove entrained and/or dissolved water. Dehydration is preferably performed by vacuum drying the composition at temperatures between 50° and 150° C, and most preferably between 70° and 100° C, at 5 to 100 mm Hg to avoid any appreciable thermal decomposition of the mixed ester product.

The invention will be better understood from a consideration of the following examples. All percentages are based upon weight unless otherwise indicated.

EXAMPLE I

Run 1

1534 grams (10 moles) of phosphorus oxychloride and 50 grams (0.38 moles) of anhydrous aluminum chloride as the catalyst were added to a 5-liter flask, stirred and heated to 50° C. 940 grams of melted phenol was then added to the flask over a 3-hour period while maintaining the temperature at 50° C. The liberated hydrogen chloride was absorbed in water and titrated with standard caustic solution to follow the course of the reaction. After the phenol was added, the temperature was maintained at 50° C with a hot water bath for an additional two hours and then rapidly increased to 60° C until less than 1% of unreacted phenol was present in the reaction mixture, approximately two hours. The reaction mixture was then cooled to room temperature, approximately 25° C. The total amount of hydrogen chloride evolved was 9.89 moles. The composition of the chloridate mixture was determined by gas chromatography to contain 10.0% phosphorus oxychloride, 72.0% phenyl phosphorodichloridate and 18.0% diphenyl phosphorochloridate.

To a 3-liter flask fitted with a stirrer, dropping funnel, reflux condenser and thermometer was charged 741 grams (10.0 moles) of n-butanol and the temperature adjusted to between 18° and 20° C. 539 [5.0 moles of phosphorus-chloride (P-Cl) equivalent] of the mixed chloridate composition was slowly fed into the flask over a 1.5 hour period. The temperature was then maintained at between 22° and 24° C until the reaction was completed, approximately 9 hours.

A 5-liter flask was charged with 960 grams of 25% sodium hydroxide solution and cooled to 5° to 10° C. The crude phosphate ester reaction mixture was slowly added to the agitated sodium hydroxide solution while keeping the temperature below 30° C and the pH value of the aqueous layer above 11.

After the reaction mixture was allowed to settle and separate into two phases, the organic phase was removed and passed into a Buchler rotary vacuum flask evaporator heated at 100° C under 10 mm Hg to recover unreacted butanol. The recovered distillate contained the unreacted butanol, 4 to 5% butyl chloride, about 10% water and less than 50 ppm phenol.

The residual mixed phosphate ester composition was then washed with 2% sodium hydroxide and allowed to settle into two phases. The organic phase was water washed at 25° C and then vacuum dried at 80° to 100° C under 10 mm Hg.

The results of product analysis are set forth in the Table.

"Color" analysis was performed according to the Gardner Color Standard as set forth in Federal Test Method No. 4248 "% TBP" is the weight percent of tributyl phosphate in the final composition. "% DBPP" is the weight percent of dibutyl phosphate in the final composition. "% BDPP" is the weight percent of butyl diphenyl phosphate in the final composition. The "R/Ar ratio" is the molar ratio of alkyl ($C_4H_9O$) groups to aryl ($C_6H_5O$) groups in the final composition measured by gas chromatography. This ratio must be in the range of 1.85 to 2.35. The "% yield" represents the amount of final composition produced based upon the amount of phosphorus oxychloride.

EXAMPLE II

Runs 2 to 8

The procedure of Example I was repeated except that the reaction between the n-butanol and the chloridates was modified according to the Table. All results are set forth in the Table.

The invention being thus described, it will be obvious that the same way be varied in many ways. Such variations are not to be regarded as a departure from the spirit and scope of the invention, and all such modifications are intended to be included within the scope of the following claims.

tion mixture to prepare a first reaction product comprising crude phenyl phosphorodichloridate, diphenyl phosphorochloridate and unreacted phosphorus oxychloride;

b. reacting the first reaction product with at least two moles of n-butanol per replaceable chloride under agitation at a temperature below 35° C for a sufficient time to prepare a second reaction product comprising crude tributyl phosphate, dibutyl phenyl phosphate, and butyl diphenyl phosphate; and c. purifying the second reactiomn product by removing acid esters, acidic impurities, salts unreacted n-butanol from the second reaction product thereby leaving a substantially pure mixed phosphate ester composition consisting essentially of 10% to 19% tributyl phosphate, 62% to 80% dibutyl phenyl phosphate, and 10% to 19% butyl diphenyl phosphate.

2. The process of claim 1 wherein the first reaction product is slowly added to the excess n-butanol under agitation at a temperature of about 15° to 20° C until the addition is complete whereupon the reaction temperature is maintained at about 20° to 30° C until the reaction is completed.

3. The process of claim 1 wherein the second reaction product is purified by contacting the second reaction product with a strong caustic solution to provide an excess of caustic at a temperature below 35° C so that the resulting aqueous phase has a pH value higher than 10.5, separating the resulting organic phase from the aqueous phase, removing by distillation unreacted n-butanol from the organic phase and washing the re-

TABLE

| | Moles of Butanol | Reaction Hold Time (hours) | Pressure | Product analysis | | | | R/AR Molar Ratio | % Yield |
|---|---|---|---|---|---|---|---|---|---|
| | | | | Color | % TBP | % DBPP | % BDPP | | |
| Example 1 Run 1 | 100 mole % | 9 | atmospheric | < 1 | 12.4 | 69.9 | 17.7 | 1.91 | 81.5 |
| Example 2 Run | | | | | | | | | |
| 2 | 100 mole % | 4 | atmospheric | < 1 | 12.3 | 69.3 | 18.4 | 1.89 | 77.0 |
| 3 | 100 mole % | 17 | atmospheric | < 1 | 12.7 | 69.2 | 18.0 | 1.94 | 77.0 |
| 4 | 200 mole % | 4 | atmospheric | < 1 | 13.3 | 70.2 | 16.6 | 1.96 | 82.0 |
| 5 | 100 mole % | 4 | vacuum | < 1 | 13.6 | 70.0 | 16.4 | 1.97 | 74.5 |
| 6 | 100 mole % | 9 | vacuum | < 1 | 12.4 | 69.4 | 18.3 | 1.89 | 76.5 |
| 7 | 200 mole % | 4 | vacuum | < 1 | 12.0 | 73.7 | 14.3 | 1.99 | 78.0 |
| 8 | 200 mole % | 9 | vacuum | < 1 | 13.7 | 70.7 | 15.6 | 2.01 | 88.5 |

What is claimed is:

1. A process for preparing a mixed phosphate ester composition consisting essentially of 10% to 19% tributyl phosphate, 62% to 80% dibutyl phenyl phosphate, and 10% to 19% butyl diphenyl phosphate, which comprises:

a. reacting phosphorus oxychloride with phenol in a molar ratio 1:0.8 to 1.0 at a temperature of about 40° to about 100° C until less than 1% unreacted phenol is present in the reaction mixture while moving liberated hydrogen chloride from the reacsidual phosphate ester product with a dilute caustic solution to remove remaining impurities.

4. The process of claim 3 wherein said second reaction product is contacted with 15 to 25 weight % caustic solution at a temperature between 0° and 30° C so that the resulting aqueous phase has a pH value above 11.0.

5. The process of claim 1 wherein the purified mixed phosphate ester composition is vacuum dried at a temperature between 50° and 150° C at 5 to 100 mm Hg.

* * * * *